(12) United States Patent
Padala et al.

(10) Patent No.: US 9,050,189 B2
(45) Date of Patent: Jun. 9, 2015

(54) METHOD AND APPARATUS FOR MINIMALLY INVASIVE HEART VALVE PROCEDURES

(75) Inventors: Sai Muralidhar Padala, Atlanta, GA (US); Ajit P. Yoganathan, Tucker, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 50 days.

(21) Appl. No.: 13/132,845

(22) PCT Filed: Dec. 4, 2009

(86) PCT No.: PCT/US2009/066849
§ 371 (c)(1),
(2), (4) Date: Aug. 26, 2011

(87) PCT Pub. No.: WO2010/065912
PCT Pub. Date: Jun. 10, 2010

(65) Prior Publication Data
US 2011/0301701 A1    Dec. 8, 2011

Related U.S. Application Data

(60) Provisional application No. 61/119,869, filed on Dec. 4, 2008.

(51) Int. Cl.
*A61F 2/24*     (2006.01)
*A61B 17/115*   (2006.01)
(Continued)

(52) U.S. Cl.
CPC ............. *A61F 2/2445* (2013.01); *A61F 2/2442* (2013.01); *A61B 17/0218* (2013.01);
(Continued)

(58) Field of Classification Search
USPC ............ 623/1.11, 2.1, 2.11, 2.36, 2.37, 2.38, 623/2.39, 2.4, 904; 606/139, 142, 148, 153; 128/898
See application file for complete search history.

(56) References Cited

U.S. PATENT DOCUMENTS 6,419,696 B1 *   7/2002   Ortiz et al. .................. 623/2.37
6,689,062 B1     2/2004   Mesallum
(Continued)

FOREIGN PATENT DOCUMENTS

WO    WO 2008/097999 A2    8/2008

OTHER PUBLICATIONS

International Search Report for corresponding International Patent Application No. PCT/US2009/066849 mailed Feb. 1, 2010.
(Continued)

*Primary Examiner* — Dianne Dornbusch
*Assistant Examiner* — Robert Lynch
(74) *Attorney, Agent, or Firm* — Merchant & Gould P.C.

(57) ABSTRACT

An apparatus (100) for and a method of delivering and implanting a surgical device on an anatomic structure is through minimally invasive procedures. The method is facilitated by an apparatus including a unitary tube (106) operatively connected to a deployment head (118) controlled by an apparatus controller. The deployment head is configured to deploy suture hooks or similar clips that connect an annuloplasty implant to heart tissue and secondary surgical devices to the annuloplasty implant. The apparatus is further configured to facilitate orientation adjustment or collapsing of the deployment head and surgical devices attached thereto in order to facilitate their passing through an incision smaller than generally required. After the deployment head passes through the incision its orientation is readjusted so that it may be positioned and the annuloplasty implant automatically sutured to a heart valve annulus by the apparatus suturing sub-assembly using the suture hooks.

19 Claims, 10 Drawing Sheets

(51) Int. Cl.
*A61B 17/02* (2006.01)
*A61B 17/00* (2006.01)
*A61B 17/064* (2006.01)

(52) U.S. Cl.
CPC .. *A61B 17/1155* (2013.01); *A61B 2017/00398* (2013.01); *A61B 2017/00402* (2013.01); *A61B 2017/0647* (2013.01); *A61F 2/2466* (2013.01)

(56) References Cited

U.S. PATENT DOCUMENTS

| | | | |
|---|---|---|---|
| 2004/0148021 A1* | 7/2004 | Cartledge et al. | 623/2.37 |
| 2004/0236419 A1* | 11/2004 | Milo | 623/2.36 |
| 2005/0055087 A1 | 3/2005 | Starksen | |
| 2006/0025750 A1 | 2/2006 | Starksen et al. | |
| 2006/0212114 A1 | 9/2006 | Menicanti et al. | |
| 2006/0271081 A1 | 11/2006 | Realyvasquez | |
| 2008/0167713 A1 | 7/2008 | Bolling | |
| 2008/0306586 A1* | 12/2008 | Cartledge et al. | 623/2.11 |
| 2009/0264903 A1* | 10/2009 | Lee et al. | 606/142 |

OTHER PUBLICATIONS

European Communication dated Aug. 6, 2013 cited in Application No. 09 765 211.9, 4 pgs.
Japanese Non-Final Office Action dated Nov. 12, 2013 cited in Application No. P2011-539759, 8 pgs.
European Office Action dated Nov. 7, 2014 cited in Application No. 09 765 211.9, 3 pgs.

* cited by examiner

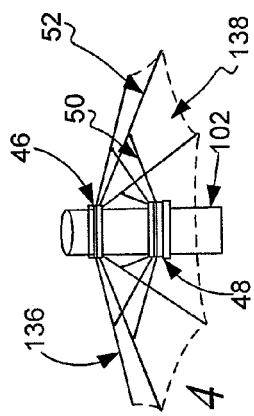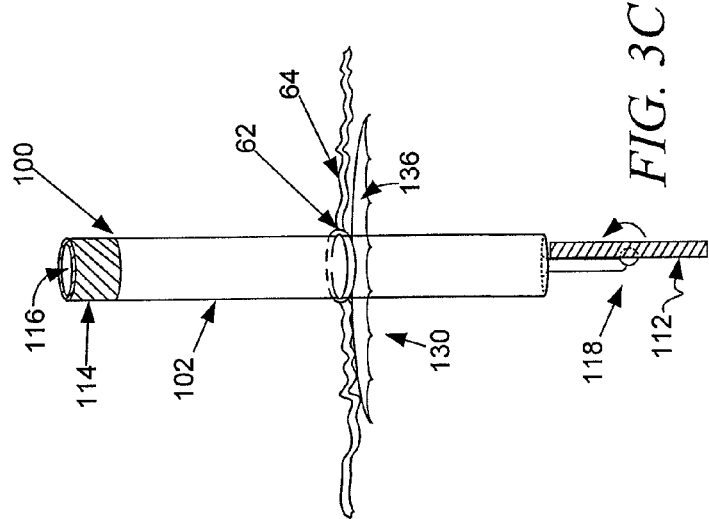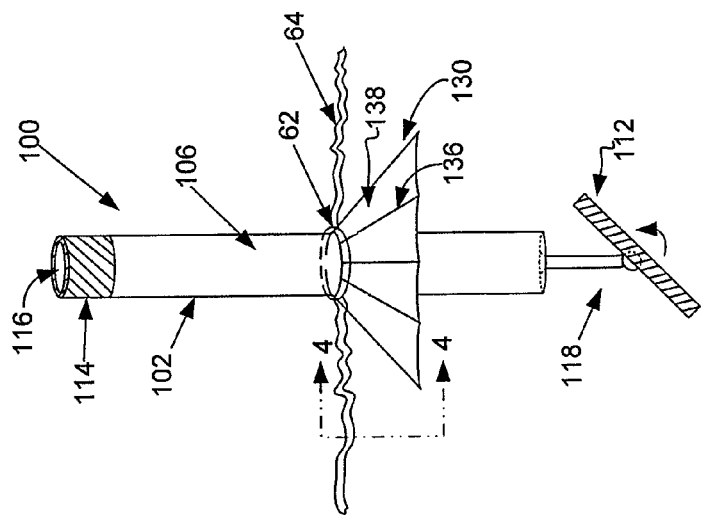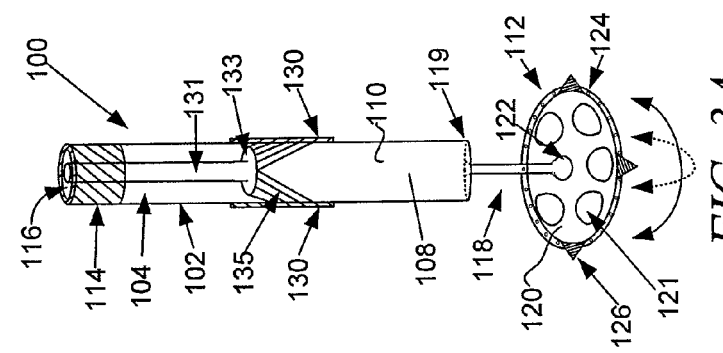

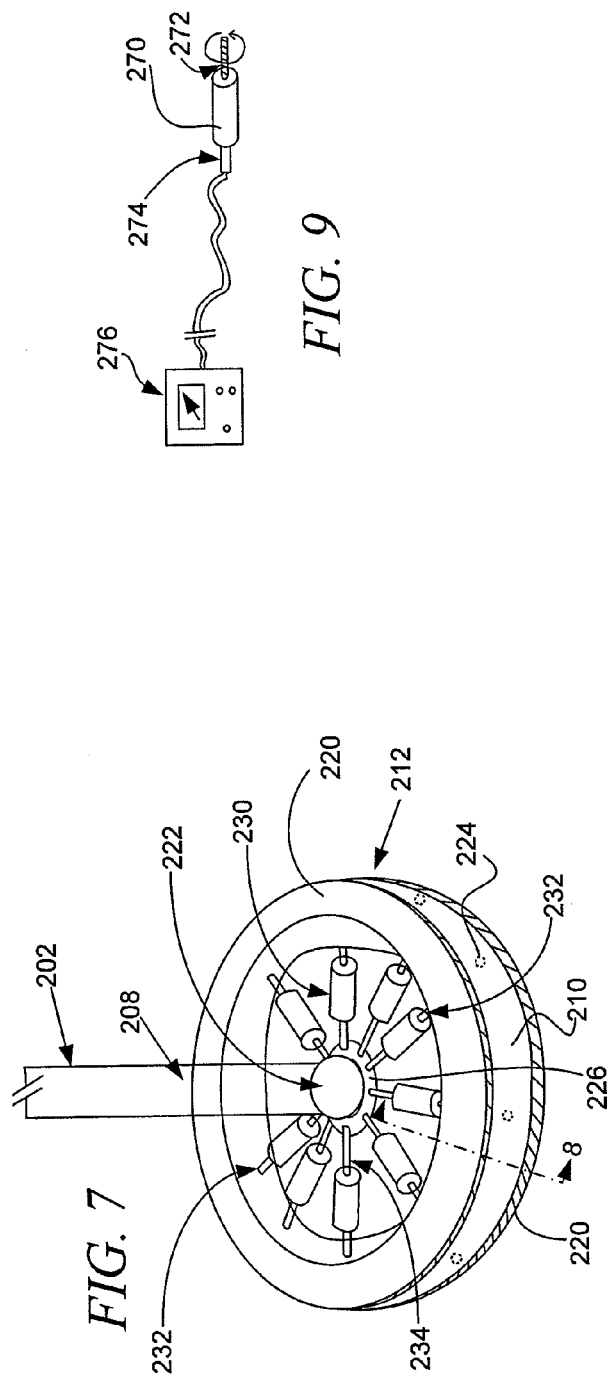
FIG. 7
FIG. 8
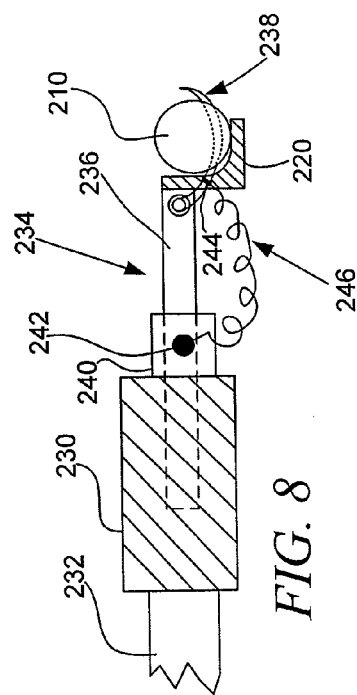
FIG. 9

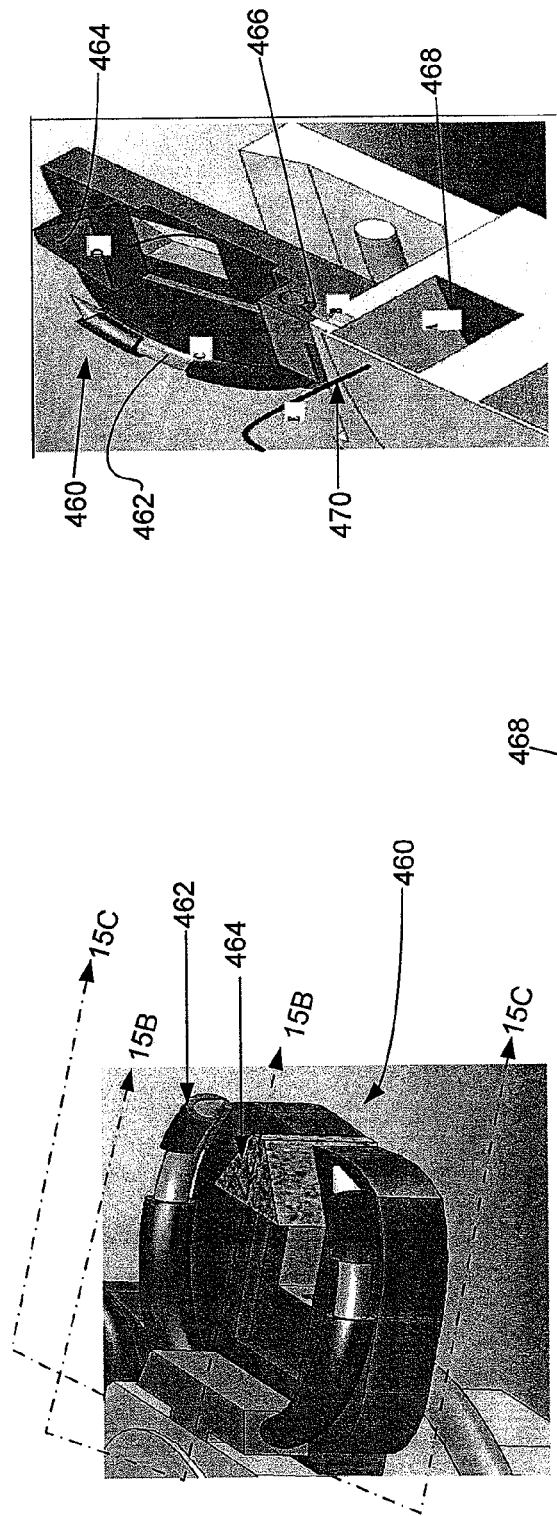
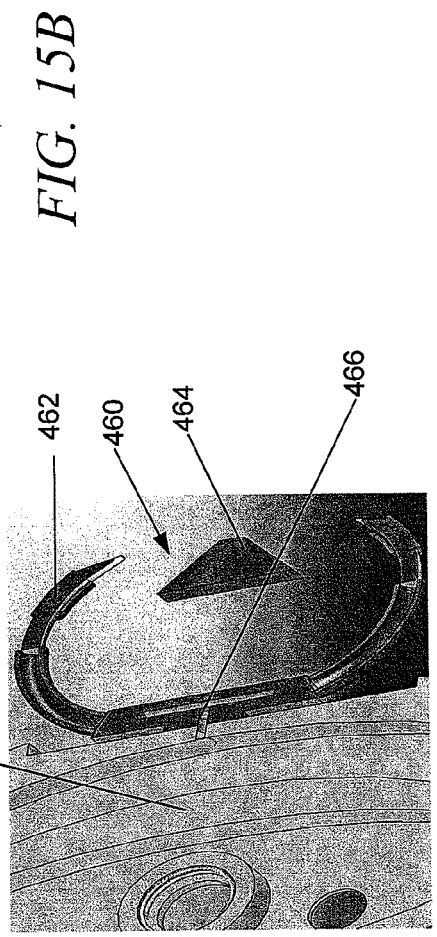
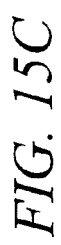
FIG. 15B
FIG. 15C
FIG. 15A

METHOD AND APPARATUS FOR MINIMALLY INVASIVE HEART VALVE PROCEDURES

CROSS-REFERENCE TO RELATED APPLICATIONS

This application is being filed on 2 Jun. 2011, as a U.S. National Stage of PCT International Patent Application No. PCT/US2009/066849, filed on 4 Dec. 2009 and claims priority to U.S. Provisional Patent Application Ser. No. 61/119,869 filed on 4 Dec. 2008 and which applications are incorporated herein by reference. To the extent appropriate, a claim of priority is made to each of the above disclosed applications.

FIELD OF INVENTION

This invention relates to devices and methods for repair and replacement of atrioventricular heart valves using minimally invasive techniques. The devices and methods described in the present invention provide effective ways to deliver an annuloplasty ring to the site of implantation with guidance from medical imaging modalities, methods to insert medical devices into a body cavity by reducing blood loss, techniques to anchor the annuloplasty ring to the tissue at the desired site and in the desired orientation, and finally deploy secondary devices such as artificial heart valves onto the annuloplasty ring.

BACKGROUND OF THE INVENTION

The heart is a hollow muscular organ with four pumping chambers: the left and right atria and the left and right ventricles. One-way valves between each of the chambers control the flow of blood in and out of the heart. The valves that control the blood flow between the atria and the ventricle are termed as Atrio-Ventricular Valves while the valves between the Ventricles and the outflow tracts are Outflow Tract/Semilunar Valves. The left atrio-ventricular valve is called the Mitral Valve, while the left ventricular outflow tract valve is called the Aortic Valve. Similarly, the right atrio-ventricular valve is called the Tricuspid Valve, while the right ventricular outflow tract valve is called the Pulmonary Valve. The atrioventricular valves, which are the mitral and tricuspid valves have four main components—the annulus which is a fibromuscular ring, the leaflets which are planar collagenous tissues (2 in mitral, and 3 in tricuspid valves), several chordae tendineae that connect the leaflets to the papillary muscles. The mitral valve regulates blood flow between the left atrium and the left ventricle, while the tricuspid valve regulates flow between the right atrium and the right ventricle. The mitral valve consists of a D-shaped annulus with two leaflets emerging from it that extend into the left ventricle. Both the leaflets are connected via collagenous chordae tendineae to the tips of the anterolateral and posteromedial papillary muscles.

Similar to the mitral valve, the tricuspid valve, illustrated in FIG. 1, has an ovoid annular shape and regulates the flow of blood between the right atrium and the right ventricle. The tricuspid valve 10 has three main components—the tricuspid annulus 12, the three leaflets 14, 16, 18 and the three papillary muscles (not shown). The annulus 12 of the valve is a fibromuscular ring from which the three leaflets 14, 16, 18 (anterior, septal and posterior) originate and regulate the flow through the valve orifice. The leaflets 14, 16, 18 extend inward into the valve or flow orifice defined by the annulus 12. There are three commissures between the three leaflets, which include an anteroseptal commissure 22, a posteroseptal commissure 24 and an anteroposterior commissure 26. Fibrous chordae tendineae extend from the three leaflets 14, 16, 18 and insert into the three papillary muscles extending from the heart muscle. The papillary muscles located in the right ventricle hold the leaflets and restrict them from collapsing into the right atrium. The tricuspid annulus 12 is an ovoid-shaped fibrous ring, which is not very prominent and is larger in the circumferential area and different in shape than the mitral valve.

Heart failure related to heart valve dysfunction is a widespread condition in which one or more of the heart valves fail to function properly. The dysfunction of the valves is mainly divided into two types: a) Valve Stenosis—wherein the effective flow orifice area of the valve is decreased due to various reasons and there is significant obstruction to the forward flow through the valve and b) Valve Incompetence—wherein the valves do not close properly and there is excessive retrograde leakage of blood when the valve is closed. Both types of these diseases have a debilitating effect on the performance of the heart and could also lead to congestive heart failure.

Surgery to repair damaged valves is the method of choice over valve replacement in the current surgical era. Surgical repair techniques involve reconstruction or controlled alteration of the geometry of the native valve using implantable devices. One of the most common repair technique used today by the surgeons to repair atrio-ventricular valve regurgitation is annuloplasty, in which, as illustrated in FIG. 2, the valve annulus 12 is geometrically stabilized or reduced in size by suturing onto the annulus 12 a prosthetic annuloplasty implant device, such as annuloplasty implant ring 30. As illustrated in FIG. 2, annuloplasty rings 12 are designed to roughly conform to the shape of the annulus 12 and maintain ample leaflet coaptation and allow good forward flow. There are also specific annuloplasty rings that have a non-physiological shape and upon implantation conform to the shape of the atrioventricular valve annulus to their non-physiological shape. These annuloplasty rings are generally made in different shapes, sizes and mechanical properties. D-shaped annuloplasty ring is the most common among the shapes with two important sub-categories being the full ring and a partial ring. The rings are also made rigid, semi-flexible and flexible that claim to allow the restoration of the native valve kinematics.

Implantation of these rings requires surgical intervention with an open-chest and the patient on cardiopulmonary bypass for a significant period. Surgical skill is of utmost importance in creating the sterna incision or thoracotomy and in opening the atrial wall to provide exposure of the valve. Due to its invasiveness and time on cardiopulmonary bypass, surgical repair of heart valves is a risky procedure and requires careful patient monitoring after the procedure. Thus, development of minimally invasive procedures to perform annuloplasty or to implant annuloplasty rings at the location of interest may decrease post-operative risk and reduce the patient mortality.

Present invention has particular relevance to the repair of dysfunctional atrioventricular valves using devices that enable minimally invasive implantation of annuloplasty rings and other devices thereof. The devices and techniques proposed in this application are intended to enable performing mitral annuloplasty through small incisions either in the right or left atria under image guidance either through ultrasound, fluoroscopy, magnetic resonance imaging or computer tomography. The technology allows for implantation of generic annuloplasty rings onto a multi-lumen catheter system for introduction and optimal alignment with the heart valve annulus, after which it is anchored to the surrounding tissue via needles, nitinol clips or sutures using a system of micro-electro-mechanical motors that can be operated from outside the patient's body.

SUMMARY OF THE INVENTION

A method and an apparatus for implantation of an annuloplasty implants into the heart of a patient, the apparatus comprises at least a unitary tube, an annuloplasty implant guide assembly and a guide assembly controller. The annuloplasty implant guide assembly is attached to the distal end of the unitary tube. The unitary tube comprises a proximal tube portion, a distal tube portion and a transition region disposed there between. The unitary tube further comprises an exterior surface defining an outside diameter and an interior surface defining an inside diameter of the unitary tube. The proximal tube portion of the unitary tube includes the guide assembly controller which is operatively connected to the annuloplasty implant guide assembly by a control mechanism that extends from the guide assembly controller through the interior of the unitary tube to the annuloplasty implant guide assembly which includes an automatic suturing sub-assembly system configured to deploy a plurality of suture hooks or similar clips that connect the annuloplasty implant to tissue within the heart. The distal end of the unitary tube includes an orientation member configured to facilitate orientation adjustment or collapsing of the annuloplasty implant guide assembly and the annuloplasty implant in response to manipulation of the guide assembly controller in order to facilitate passing the annuloplasty implant through an incision having a size smaller than necessary when the implant guide assembly and the annuloplasty implant are not rotated or collapsed. After the implant guide assembly and the annuloplasty implant have passed through the incision, the controller is used to readjust the orientation of the implant guide and the implant so that it may be positioned and sutured to a heart valve annulus upon initiation of automatic suturing sub-assembly system.

BRIEF DESCRIPTION OF THE DRAWINGS

Non-limiting and non-exhaustive embodiments are described with reference to the following figures, wherein like reference numerals refer to like parts throughout the various views unless otherwise specified.

FIG. 3A perspective view an embodiment of an apparatus for implantation of an annuloplasty implant into the heart of a patient, of the present invention;

FIG. 3B side view an embodiment of an apparatus for implantation of an annuloplasty implant into the heart of a patient including an incision cover, of the present invention;

FIG. 3C side view an embodiment of an apparatus for implantation of an annuloplasty implant into the heart of a patient including an incision cover, of the present invention;

FIG. 4 is section view of FIG. 3B, illustrating the incision cover;

FIG. 7 is a side view of another alternative embodiment of a modified annuloplasty implant guide assembly of the present invention;

FIG. 8 is a partial side view of a portion of the embodiment of the annuloplasty implant guide assembly of illustrated in FIG. 7;

FIG. 9 is an illustration of the components of the MEMS motor assembly utilized in the annuloplasty implant guide assembly illustrated in FIG. 7;

FIG. 15A is perspective view of a suturing sub assembly of the present invention;

FIG. 15B is a sectional view of the suturing sub assembly illustrated in FIG. 15A; and FIG. 15C is a sectional view of the suturing sub assembly illustrated in FIG. 15A;

GENERAL DESCRIPTION OF THE INVENTION

Figure 1:
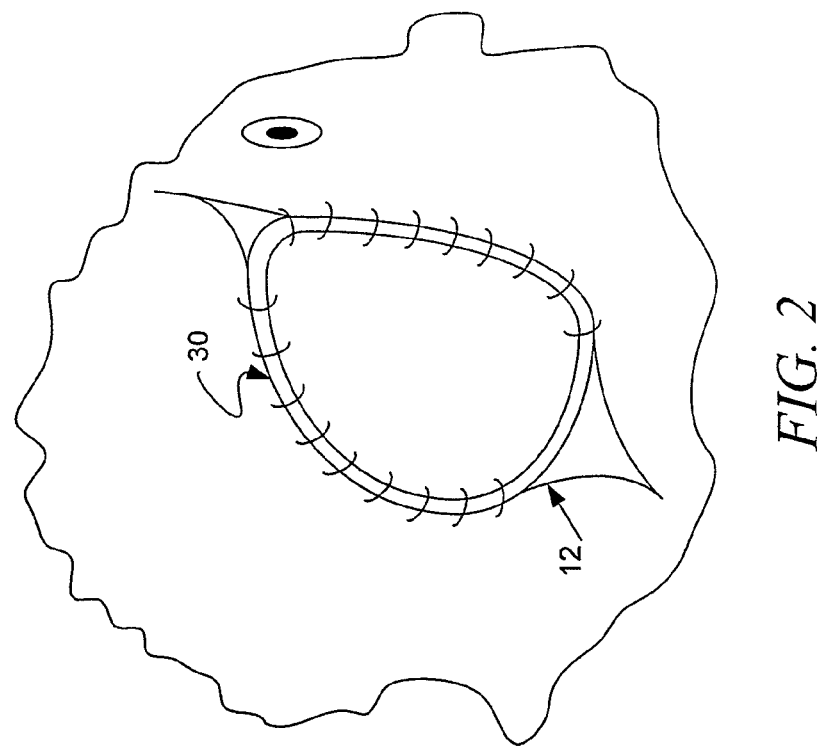
FIG. 1 is a plan view of a heart valve and surrounding anatomy.
Figure 2:
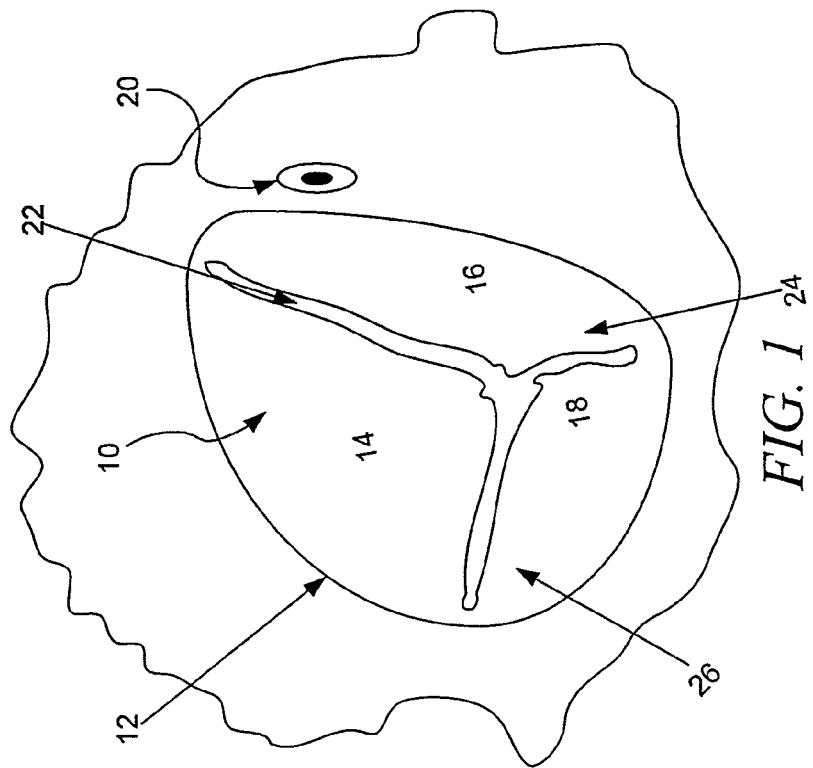
FIG. 2 is plan view of a heart valve including an annuloplasty implant ring.

Various embodiments are described more fully below with reference to the accompanying drawings, which form a part hereof, and which show specific embodiments of the invention. However, embodiments may be many different forms and should not be construed as limited to the embodiments set forth herein; rather, these embodiments are provided so that this disclosure will be thorough and complete, and will fully convey the scope of the invention to those skilled in the art. Accordingly, the following detailed description is, therefore, not to be taken in a limiting sense.

The present invention describes a system and method for implantation of generic annuloplasty rings and other surgical devices, onto a heart valve annulus or other anatomic orifices through minimally invasive procedures. More specifically, the present invention comprises an annuloplasty system and method to repair of dysfunctional heart valve. Current standards of care for treatment of patients with heart valve disorders require an open-heart operation in which the patient is put on cardiopulmonary bypass. The procedure involves risk to the patient's health and is associated with increased mortality. The present invention discloses a system and method to perform heart valve repair through a small incision through which an annuloplasty implant guide assembly is utilized to deliver and implant an annuloplasty implant within a beating heart. The annuloplasty implant guide assembly of the present invention discloses four sub-systems that are configured for use in minimally invasive surgical procedures, including: (1) an external shape adjustment system; (2) an annuloplasty ring delivery system; (3) automated suturing and anchoring system; and (4) temporary adjustable annulus system.

The external shape adjustment system is comprised of a set of trocar devices that are used to reduce the shape of the valve annulus by applying pressure to the external circumference of the annular region of the heart between the atrium and ventricle. Upon reducing the annulus to a significantly smaller size, an embodiment of an annuloplasty implant delivery system is used to deliver an annuloplasty implant through a small incision and the implant is positioned onto the valve annulus through image guidance from a biomedical imaging modality.

The annuloplasty implant delivery system is comprised of a hollow unitary tube, an annuloplasty implant guide assembly and a guide assembly controller. The annuloplasty implant guide assembly, which includes a suturing sub-assembly system is configured with a self-deployment mechanism to facilitate deployment of a plurality of suture hooks that connect the annuloplasty implant to the heart, is attached to the distal end of the unitary tube which is comprised of a proximal tube portion, a distal tube portion and a transition region disposed there between. The proximal tube portion of the unitary tube shall be configured to include the guide assembly control mechanism which in one embodiment comprises a pulley system having a control wire extending through the interior of the unitary tube and connecting to the annuloplasty implant guide assembly. The orientation of the annuloplasty implant guide assembly may be manipulated by the control wire through rotation of the guide assembly control plate that is integrated into the annuloplasty implant guide assembly as a portion of the proximal tube portion of the unitary tube.

In one embodiment of the invention, the distal end of the unitary tube includes an orientation member configured to facilitate rotation of the annuloplasty implant guide assembly in a manner such that its longest side is perpendicular with the plane of the body into which an incision has been made. This causes the annuloplasty ring which is removably attached to the annuloplasty implant guide assembly to be delivered in a side-on orientation, thereby minimizing the cross-sectional size of the annuloplasty ring. In this embodiment, the annuloplasty implant guide assembly has an annular shape and contains a suturing sub-assembly that includes a plurality of suture hooks configured to detach from the suturing sub-assembly and connect the annuloplasty implant ring to the annulus of a heart valve. In another embodiment, the annuloplasty implant guide assembly includes an implant delivery member comprised of a plurality of arms each of which are attached to the annuloplasty implant being delivered to the heart. The implant delivery member is configured to facilitate folding of a flexible annuloplasty implant in order to facilitate passing the annuloplasty implant through an incision having a size smaller than necessary when the annuloplasty implant is not folded.

The attachment system of the annuloplasty implant guide assembly is comprised of a suturing sub-assembly system including a deployment head and a plurality of suture hooks configured to detach from the deployment head and connect the annuloplasty implant to the heart. The attachment system also includes a deployment mechanism extending through the interior surface of the unitary tube, wherein the deployment mechanism includes at least a string that engages each of the plurality of suture hooks thereby hooking the annuloplasty implant directly to tissue within the heart through the suture hooks upon pulling the string out through the interior of the unitary tube. In another embodiment, the deployment mechanism may be automatic and contained within the implant delivery member. In one embodiment, the plurality of suture hooks are releasably attached to the deployment mechanism and comprised of a first hook arm and a second hook arm, wherein the first and second hook arms are both pivotally connected at a first end by a pivot pin, and the second ends of the first and second hook arms are configured to facilitate easy extension through tissue of an annulus wall within a heart valve and easy extension through an annuloplasty implant thereby connecting the annuloplasty implant to the annulus of a valve. The second ends of the first and second hook arms also structured to facilitate a latching connection that causes the second ends of the first and second hook arms to create a substantially continuous closed loop upon connecting the second ends of the first and second hook arms. It is contemplated that the annuloplasty implant guide assembly may include an adjustable mounting system onto which annuloplasty rings of a plurality of different shapes and sizes may be mounted for delivery during a minimally invasive surgical procedure.

In another embodiment, the suturing sub-assembly of the annuloplasty implant guide assembly includes a plurality of pumps, wherein the pumps may be microfluidic, microelectromechanical or some other pumping configuration that facilitates pumping action at the micro level. In this embodiment, each of the plurality of pumps is operatively connected to at least one of the plurality of suture hooks and control deployment of the suture hooks which causes a connection of the annuloplasty implant to the inner tissue of the heart cavity into which the annuloplasty implant is being inserted.

A plurality of microfluidic pumps position, wherein each of the plurality of microfluidic pumps is connected to at least one of the plurality of a suture hooks. The microfluidic pumps control deployment and locking of the suture hooks onto the annuloplasty implant into position within the patient heart.

In another embodiment, the annuloplasty implant guide assembly is configured to include an incision cover assembly. The incision cover assembly is attached to the exterior surface of the unitary tube and comprises umbrella skeleton, covered by an incision cover material, which is connected to the exterior surface of the unitary tube. The umbrella skeleton comprises at least a deployment ring and deployment arms attached thereto. Sliding the ring up and down the exterior surface of the unitary tube facilitates opening and closing of the incision cover.

It is contemplated that a three dimensional echocardiogram may be used to assist a surgeon, following insertion of the delivery system through a small incision, in positioning an annuloplasty implant over a valve annulus during a minimally invasive operation. Thus allowing the device to be implanted without opening the patient's chest. Upon delivering an annuloplasty ring to the correct position, an automated suturing/anchoring system within the annuloplasty implant guide assembly is used to place permanent sutures/anchors (hooks) at multiple locations along the circumference of the annulus, whereby hooks are deployed directly though the ring and tissue. In one embodiment, the hooks are comprised of NiTinol or stainless steel. It is contemplated that the hooks may be comprised of any material durable enough to create hooks that hooks are deployed directly though the ring and tissue.

In another embodiment, the annuloplasty implant guide assembly further is configured to include a clamping assembly that facilitates resizing of a valve annulus. The clamping assembly comprising a top clamp plate and a bottom clamp plate, and a clamping assembly extending between the top clamp plate and the bottom clamp plate that facilitates reduction of spacing between the top clamp plate and the bottom clamp plate.

The method of using the annuloplasty implant guide assembly to install an annuloplasty implant involves providing an annuloplasty implant guide assembly configured with at least one annuloplasty implant connector to which the annuloplasty ring is connected. Using the guide assembly controller, the orientation of the implant guide assembly is adjusted, which causes adjustment of the orientation of the annuloplasty implant in order to facilitate passing of the annuloplasty implant through an incision on a patient's body that has a size smaller than the size required when the annuloplasty implant orientation is not adjusted. After extending the orientation adjusted guide assembly and the annuloplasty ring through the incision, the orientation of the guide assembly and thereby the orientation of the annuloplasty ring is readjusted and the annuloplasty ring is positioned within a heart valve annulus. Next, an automatic suture procedure is initiated, wherein at least one of a plurality of suture connection hooks are engaged causing an end of the suture connection hook to pass through tissue of the heart valve annulus and the annuloplasty ring and thereby connect the annuloplasty ring to the heart valve annulus.

In one embodiment of this system and method, an adjustable annuloplasty system is first temporarily implanted onto the valve annulus that is used to tether the annular sutures/anchors towards the anchoring hooks placed on the annuloplasty ring. Finally, after the valve annulus is hooked onto the annuloplasty rings the internal and external delivery systems are retracted out of the patient's body and a simple plug closure system is left in the incision to allow air bubbles to escape, and a zipper system is used to close the incision.

The embodiments of the present invention as shown in the accompanying figures and described herein are particularly designed for or relate to the repair and replacement of atrioventricular heart valves using minimally invasive techniques. However, the present invention is not limited for application to the repair and replacement of atrioventricular heart valves, and it is contemplated that variations of the embodiments may apply to other heart valves and other minimally invasive surgical techniques.

DETAILED DESCRIPTION OF EMBODIMENTS OF THE INVENTION

Referring now to FIGS. 3A, 3B and 3C, the invention illustrated comprises an adjustable apparatus 100 for implantation of an annuloplasty implant. The apparatus 100 is comprised of a unitary tube 102, an annuloplasty guide assembly 112, a guide assembly controller 114 and an orientation member 118. The annuloplasty implant guide assembly 112 is attached to the distal end of the unitary tube 102 by the orientation member 118. The unitary tube 102 is comprised of a proximal tube portion 104, a transition region 106 and a distal tube portion 108. The unitary tube 102 is configured with an exterior surface 110 defining an outside diameter and an interior surface 116 defining an inside diameter of the unitary tube 102. The proximal tube portion 104 of the unitary tube 102 includes the guide assembly controller 114 which is operatively connected to the annuloplasty implant guide assembly 112 by a control mechanism that extends from the guide assembly controller through the interior of the unitary tube 102 to the annuloplasty implant guide assembly 112 which includes an automatic suturing sub-assembly system configured to deploy a plurality of suture hooks that connect the annuloplasty implant to tissue within the heart.

Orientation member 118 which is configured to facilitate orientation adjustment or steering of the annuloplasty implant guide assembly 112 and thereby orientation adjustment of an attached annuloplasty implant. The adjustment of the orientation or steering of annuloplasty implant guide assembly 112, as illustrated in FIGS. 3A, 3B, and 3C, occurs in response to manipulation of the guide assembly controller 114 and is done in order to facilitate passing the annuloplasty implant guide assembly 112 and the attached annuloplasty implant through an incision 62 on a body 64 that has a size that is smaller than necessary when the implant guide assembly is not rotated. In situations where a straight incision has been made, annuloplasty implant guide assembly 112 is rotated so that it has a side-on orientation which minimizes its cross-sectional size. After the implant guide assembly and the annuloplasty implant have passed through the incision, the guide assembly controller 114 is used to readjust the orientation of the annuloplasty implant guide assembly 112 and the attached annuloplasty implant so that the implant may be positioned and sutured to a heart valve annulus upon initiation of automatic suturing sub-assembly system.

It is contemplated that unitary tube 102 of the present invention may comprise a unique configuration in order to perform certain aspects of the embodiments described herein. However, some embodiments, such as the embodiment illustrated in FIG. 3A, unitary tube 102 may be a multiple lumen catheter. As the embodiment illustrates in FIG. 3A, unitary tube 102 includes an inner cylinder 131, which in some embodiments may also be a catheter. Unitary tube 102 also includes an incision cover assembly 130. In the embodiment of the apparatus 100 illustrated in FIG. 3A, the inner cylinder 131 is a translatable and rotatable arm, one end of which is connected to the guide assembly controller 114 and the other end is connected to an umbrella skeleton deployment ring 133, which is connected to a frame of spars 135 within and extending through the unitary tube 102 to connect to the umbrella skeleton 130.

Another embodiment of the incision cover assembly 130 is illustrated in FIGS. 3B, 3C and 4. In this embodiment, the incision cover assembly 130 is attached to the exterior surface of the unitary tube 102 and comprises an umbrella skeleton 136, covered by a biocompatible incision cover material 138. The umbrella skeleton 136 comprises at least a stabilizing ring 46, a deployment ring 48 and deployment arms 50 and 52. The deployment ring 48 is configured to slide up and down the exterior surface of the unitary tube 20 and thereby facilitate opening and closing of the incision cover 30.

Referring back to FIG. 3A, the distal end 119 of the unitary tube 102 includes an opening on its distal end and allows for introduction of other surgical implant devices through the unitary tube 102 into the body cavity. The distal end of the unitary tube 102 is attached to the annuloplasty implant guide assembly frame 120 by an orientation member 118, which provides a link between the guide assembly controller 114 and the annuloplasty implant guide assembly 112 and includes at least a orientation bearing system 122 centrally located on the annuloplasty implant guide assembly frame 120 to which an annuloplasty implant device, such as an annuloplasty ring would be attached. The annuloplasty implant guide assembly frame 120 is also configured with a grooved area 124 along its circumference that facilitates positioning of an annuloplasty implant on the guide assembly frame 120.

The functional capabilities of apparatus 100 facilitates the process of making a real-time incision on the outer surface of the body cavity, introduction of a portion of apparatus 100 into the incision 62, as illustrated in FIGS. 3B and 3C, with the assistance of sharp incision ends 126 mounted on the annuloplasty implant guide assembly frame 120 having a medical implant device, such as an annuloplasty ring mounted thereon. The incision ends 126 may be mounted on a specific location of the annuloplasty implant guide assembly frame 120 in order to facilitate making an incision of a particular dimension on the body cavity to insert the apparatus 100. The annuloplasty implant guide assembly 112 is rotatable by way of the orientation bearing system 122 which facilitates rotation of the annuloplasty implant guide assembly 112 and the attached annuloplasty implant in 360 degree planes with infinite degrees of freedom as illustrated in FIGS. 3A, 3B, and 3C, in response to manipulation of the guide assembly controller 114. The ability to rotate the annuloplasty implant guide assembly 112 and the attached annuloplasty implant in infinite degrees of freedom allows the user to determine the most optimal way of inserting the annuloplasty implant guide assembly 112 and the attached annuloplasty implant into the body through the smallest incision possible. Rotation can be performed before or after insertion of the annuloplasty implant guide assembly 112 into the body cavity. Rotation of the annuloplasty implant guide assembly 112 may be done before insertion of the annuloplasty implant guide assembly 112 into the body in order to reduce the size of the incision required for the annuloplasty implant guide assembly 112 to pass through the body. Generally, rotation of the annuloplasty implant guide assembly 112 would be such that so that its longest side is perpendicular with the plane of the body into which an incision has been made. FIG. 3C illustrates such a rotation of the annuloplasty implant guide assembly 112.

Upon creating an incision and inserting a portion of the apparatus 100 into the body 64, the incision cover assembly 130 in deployed in order to prevent the loss of blood through the incision 62. FIG. 3B illustrates the incision cover assembly 130 partially deployed. FIG. 3C illustrates the incision cover assembly 130 fully deployed. As illustrated, when the incision cover assembly 130 is fully deployed, it covers the incision 62 from the inside the cavity, thereby preventing blood loss.

The annuloplasty implant guide assembly frame 120 includes a plurality of suture hook openings 128 around its perimeter, facilitating deployment of a plurality of hooks, needles or nitonol screws by a suturing sub-assembly system through suture hook openings 128 and thereby mounting an annuloplasty implant ring to tissue within the heart. It is also contemplated that the annuloplasty implant guide assembly frame 120 may be configured in a manner that facilitates mounting sutures, clips and needles directly onto the edge of the annuloplasty implant guide assembly frame 120. Annuloplasty implant guide assembly frame 120 is also configured with a plurality of orifices 121 which may be used to introduce other sheaths, catheters, or balloon catheters into the body cavity following introduction of the other implantable devices through unitary tube 102. The annuloplasty implant guide assembly frame 120 may be of a plurality of shapes. The annuloplasty implant guide assembly 112 may be locked into or dislodged from the unitary tube 102 and interchanged as per the shape of the desired implant device to be delivered into the body cavity.

Figure 5C:
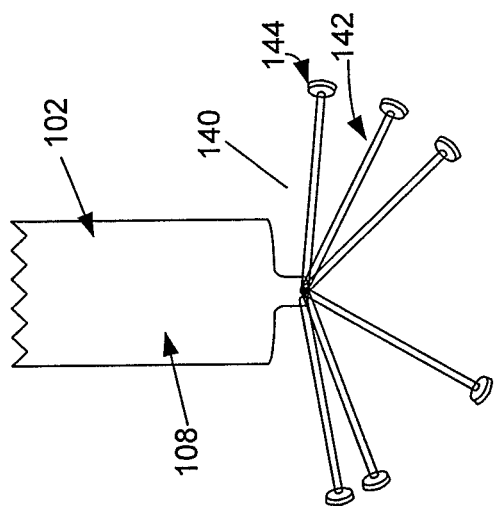
FIG. 5C is a partial side view of an alternative embodiment of an apparatus for implantation of an annuloplasty implant into the heart of a patient illustrating the assembly arms of a modified annuloplasty implant guide assembly of the present invention.
Figure 5B:
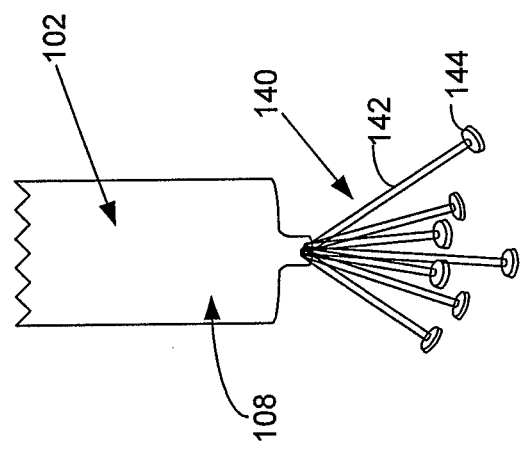
FIG. 5B is a partial side view of an alternative embodiment of an apparatus for implantation of an annuloplasty implant into the heart of a patient illustrating the assembly arms of a modified annuloplasty implant guide assembly of the present invention.
Figure 5A:
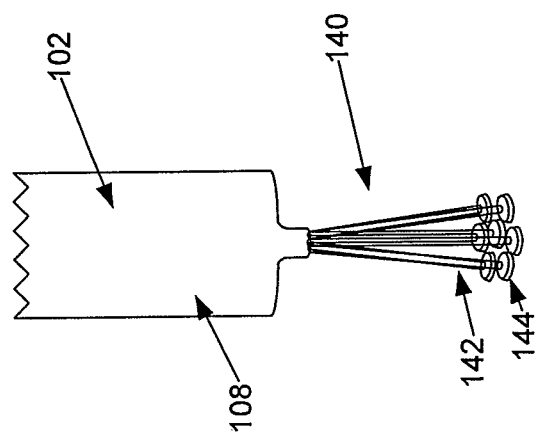
FIG. 5A is a partial side view of an alternative embodiment of an apparatus for implantation of an annuloplasty implant into the heart of a patient illustrating the assembly arms of a modified annuloplasty implant guide assembly of the present invention.

The embodiment illustrated in FIGS. 3A, 3B, and 3C is generally used to insert rigid annuloplasty rings. However, because annuloplasty rings come in a variety forms ranging for extremely rigid to extremely flexible, an embodiment specifically configured for use with flexible rings was also created and is illustrated in FIGS. 5A, 5B and 5C. As illustrated in the embodiment shown in FIGS. 5A, 5B and 5C, the distal portion 108 of the unitary tube 102 is configured with a modified annuloplasty implant guide assembly 140, comprised of a plurality of assembly arms 142 each having a connector 144 that attaches to an annuloplasty ring. The embodiment of the annuloplasty implant guide assembly 140 illustrated in FIGS. 5A, 5B and 5C facilitates implantation of an annuloplasty ring through a much smaller incision than the incision needed when implantation is performed by the embodiment of the annuloplasty implant guide assembly 112 illustrated in FIGS. 3A, 3B and 3C because, when the annuloplasty ring is flexible, referring to FIGS. 5A, 5B and 5C it may mounted onto connectors 144 on the distal ends of the plurality of assembly arms 142 and folded inward. After the annuloplasty implant guide assembly 140 and the distal portion 108 of the unitary tube 102 is inserted into the body, the guide assembly controller 114 may be manipulated and or turned, causing the plurality of assembly arms 142 to open up in the manner illustrated in FIGS. 5B and 5C and extend to the desired position.

Figure 6C:
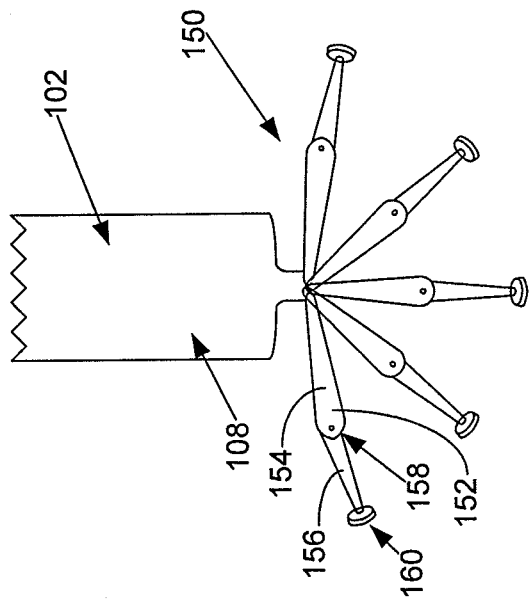
FIG. 6C is a partial side view of another alternative embodiment of an apparatus for implantation of an annuloplasty implant into the heart of a patient illustrating two piece assembly arms of a modified annuloplasty implant guide assembly of the present invention.
Figure 6B:
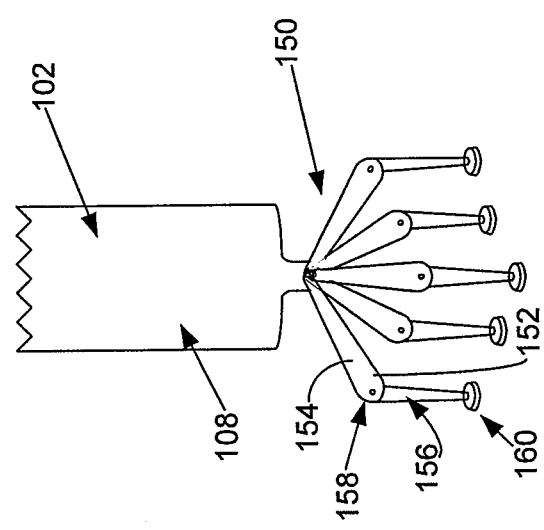
FIG. 6B is a partial side view of another alternative embodiment of an apparatus for implantation of an annuloplasty implant into the heart of a patient illustrating two piece assembly arms of a modified annuloplasty implant guide assembly.
Figure 6A:
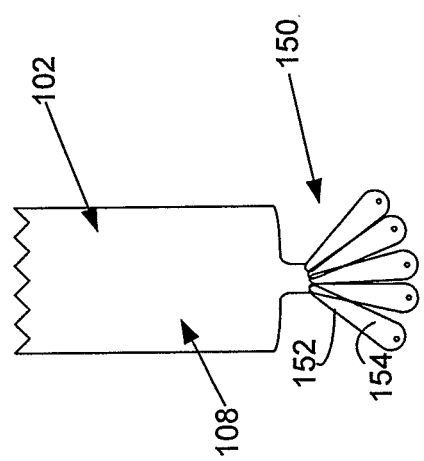
FIG. 6A is a partial side view of another alternative embodiment of an apparatus for implantation of an annuloplasty implant into the heart of a patient illustrating two piece assembly arms of a modified annuloplasty implant guide assembly of the present invention.

Another embodiment of the invention which may be used for the insertion of flexible annuloplasty rings is illustrated in FIGS. 6A, 6B and 6C. In this embodiment, the annuloplasty implant guide assembly 150 is comprised of a plurality of assembly arms, each 152 of which comprises a top arm portion 154 and a bottom arm portion 156 connected by a hinge pin 158 which facilitates a hinge like collapse or folding of each assembly arm 152 as illustrate in FIGS. 6A, 6B and 6C. As illustrated in FIG. 6a, the bottom arm portion 156 may be completely collapsed onto the top arm portion 154, or partially collapsed as illustrated in FIG. 6B, or fully extended as illustrated in FIG. 6C. This configuration allows for the annuloplasty implant guide assembly 150 to fold an annuloplasty implant to a size smaller than that which may be performed by the annuloplasty implant guide assembly 140 illustrated in FIGS. 5A, 5B and 5C. When implantation is performed by the embodiment of the apparatus illustrated in FIGS. 6A, 6B and 6C which includes an annuloplasty implant guide assembly 150, it may mounted onto the distal ends of each 152 of the plurality of assembly arms by connectors 160 and folded inward. After the annuloplasty implant guide assembly 150 and the distal portion 108 of the unitary tube 102 is inserted into the body, the guide assembly controller 114 may be manipulated and or turned, causing each 152 of the plurality of assembly arms to open up in the manner illustrated in FIGS. 6B and 6C and extend each 152 of the plurality of assembly arms to the desired position.

FIG. 7 illustrates another embodiment of an annuloplasty implant guide assembly 212, attached to the distal portion 208 of a unitary tube 202, which includes an orientation bearing system 222 that facilitates rotation of the embodiment of the annuloplasty implant guide assembly 212 and the attached annuloplasty implant ring 210 in 360 degree planes with infinite degrees of freedom, similar to the freedom of the annuloplasty implant guide 112 illustrated in FIGS. 3A, 3B, and 3C. Annuloplasty implant guide assembly 212 rotation also occurs in response to manipulation of a guide assembly controller configured on the end of the apparatus unitary tube 202. The annuloplasty implant guide assembly 212 is further comprised of an annuloplasty implant guide assembly frame 220, a MEMS motor 230 attached to a motor stabilizing ring 226 by a motor stabilizing arm 234. In this embodiment, annuloplasty implant guide assembly frame 220 is rigid and holds the annuloplasty implant ring 210 in position. The motor 230 is also attached to a suture hook deployment arm 232 which facilitates deployment of a plurality of suture hooks or needles, each of which is connected to a suture hook deployment arm 232 and aligned with one of a plurality of suture hook openings 224 and extends partially into the annuloplasty implant 210. Deploying a suture hook through one of the plurality of suture hook openings 224 configured into the annuloplasty implant guide assembly frame 220, causes the suture hook to also extend through the annuloplasty implant ring 210, into tissue within the heart and then back into the annuloplasty implant ring 210. Deployment of a suture hook is performed by releasing a spring temporarily attached to a portion of a suture hook. Following deployment of the plurality of suture hooks, the annuloplasty implant guide assembly 212 may be removed from the incision following the release of the annuloplasty implant ring 210 which is attached to tissue within the heart.

FIG. 8 illustrates a cross sectional view of a portion of the annuloplasty implant guide assembly 212, illustrating a suture hook deployment arm 232, a MEMS motor 230, a motor stabilizing arm 234, a suture hook 238 and the annuloplasty implant ring 210 which the suture hook 238 extends through. As illustrated, the annuloplasty implant ring 210 is positioned on the guide assembly frame 220 and the suture hook 238 is spring loaded, wherein spring 246 has a first end attached 242 to a movable linear body 240 which moves linearly along suture hook connection arm 236. The second end of spring 246 is attached to a connector 244 positioned on the suture hook 238. Movable linear body 240 moves linearly along the axis of the motor as a result of the motor turning the suture hook connection arm 236, which is screw threaded. The interior of movable linear body 240 is also screw threaded and matingly engages the screw threads of the suture hook connection arm 236, thereby resulting in linear movement of the moveable linear body 242 along the axis of the motor 230. This linear movement of the moveable linear body 242 determines the tension in the spring 246 and thereby the position and turning angle of the suture hook 238. FIG. 9 is an illustration of the MEMS motor 270 used in the embodiment illustrated in FIGS. 7 and 8, wherein a power supply 276 supplies power to the MEMS motor 270 which causes the turnable screw threaded shaft 272 to turn, thereby initiating linear movement of the linear movable body based on the direction that the screw threaded shaft 272 is turning.

Figure 10:
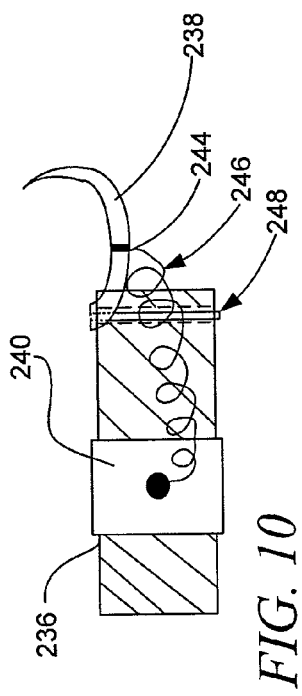
FIG. 10 is a sectional view of a portion of the hook sutures of the present invention.

Referring to FIG. 10, the suture hook 238 is connected to the suture hook connection arm 236 by a shaft 248, which slides downward instead of linearly through a pin opening, causing the suture hook to slide off of shaft 248, thereby causing automatic detachment of the suture hook and thereby completing automatic deployment of a plurality of suture hooks 238. The shaft 248 slides downward following deployment of the suture hook 238, to facilitate automatic detachment of the suture hook 238 from the suture hook connection arm 236 and thereby automatic detachment of the suture hook 238 from the suturing sub-assembly system of the apparatus 100.

Figure 11A:
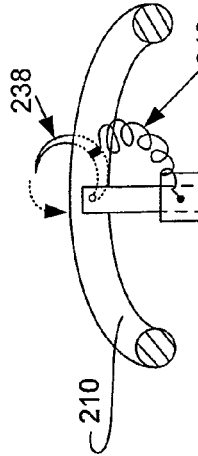
FIG. 11A illustrates the interaction of an annuloplasty implant guide assembly hook suture with an annuloplasty implant ring prior to deployment of the hook suture in accordance with the present invention.
Figure 11B:
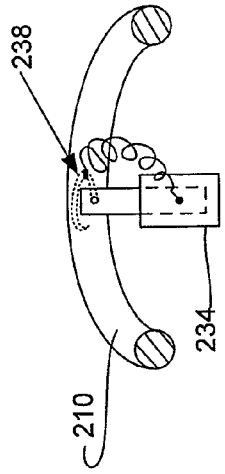
FIG. 11B illustrates the interaction of an annuloplasty implant guide assembly hook suture with an annuloplasty implant ring during deployment of the hook suture in accordance with the present invention.
Figure 11C:
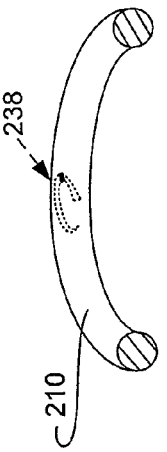
FIG. 11C illustrates the interaction of an annuloplasty implant guide assembly hook suture with an annuloplasty implant ring after deployment of the hook suture.

FIGS. 11A, 11B, 11C illustrates deployment of the suture hook 238 through the annuloplasty implant ring 210 and tissue as the suture hook 238 connects the annuloplasty implant ring 210 to tissue within the heart. FIG. 11A illustrates positioning of the suture hook 238 when the spring 246 is under tension, causing the suture hook 238 not to deploy. Upon the release of some of the tension, as illustrated in FIG. 11B, when the motor stabilizing arm 234 moves linearly towards the annuloplasty implant guide assembly frame 220, tension in the spring is released, causing the suture hook 238 to deploy through the annuloplasty implant ring 210 and tissue and back through the annuloplasty implant ring as a result of the shape of the suture hook 238 and the manner in which it pivots around the shaft 248. FIG. 11C illustrates full deployment of the suture hook 238 into the annuloplasty implant 210 following detachment of the suture hook 238 from the suture hook connection arm 236. In the embodiment illustrated, the curvature of suture hook 238 is such that suture hook 238 cannot go backwards and thereby hold the tissue and the annuloplasty implant ring 210 together.

Figure 12:
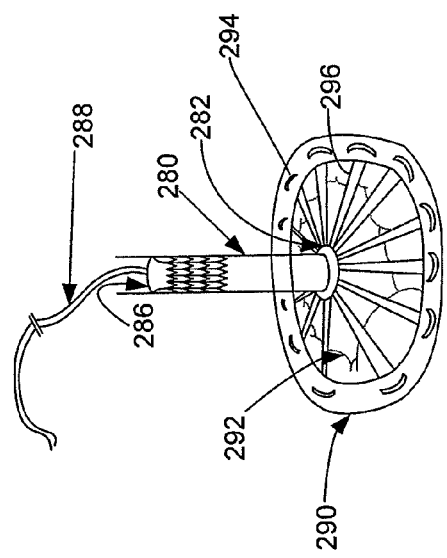
FIG. 12 is a perspective view of another alternative embodiment of an apparatus for implantation of an annuloplasty implant into the heart of a patient illustrating a modified annuloplasty implant guide assembly.

FIG. 12 is an illustration of another embodiment of the invention which is configured in a manner to facilitate delivery of other surgical implant devices to a heart valve 292 following the implantation of an annuloplasty implant ring 290 into to a heart valve annulus by suture hooks 294. As illustrated, other surgical devices, such as a heart valve 286, may be delivered to the heart valve in need of repair through the unitary tube 280, which in other embodiments may be a catheter, and then connected to the annuloplasty implant ring 290. As illustrated, the annuloplasty implant guide assembly frame 296 remains in position following deployment of the suture hooks 294 connecting the annuloplasty implant ring 290 into to a heart valve annulus. The partially extended heart valve 286 is being delivered through the unitary tube 280 of the apparatus by a partially extended guide wire 288 which pushes the partially extended heart valve 286 down through the unitary tube 280, and then down into the body cavity and into the heart valve 292 where the annuloplasty implant ring 290 is implanted. Next a balloon catheter could be used to move the heart valve 286 into position and expand the valve 286 and connect it with its valve arms to the annuloplasty implant ring 290 which was previously implanted. The previously implanted the annuloplasty implant ring 290 serves as a platform that can support implantation of the secondary devices, such as heart valve 286, within the heart valve annulus.

As illustrated in FIG. 3A, the annuloplasty implant guide assembly frame is composed of an annular shaped tapered device. In an alternative embodiment, the annuloplasty implant guide assembly frame may contain an annulus clamping and suturing sub-assemblies. As was the case with the apparatus illustrate in FIG. 3A, wherein the unitary tube 202 could be substituted for a catheter, the embodiments of the annuloplasty implant guide assembly frame containing an annulus clamping and suturing sub-assemblies shall be used in conjunction with an endoscopic catheter, currently available on the market, in combination with a peristaltic pump system that sends pressure pulses that manipulate the device's functions.

Figure 13:
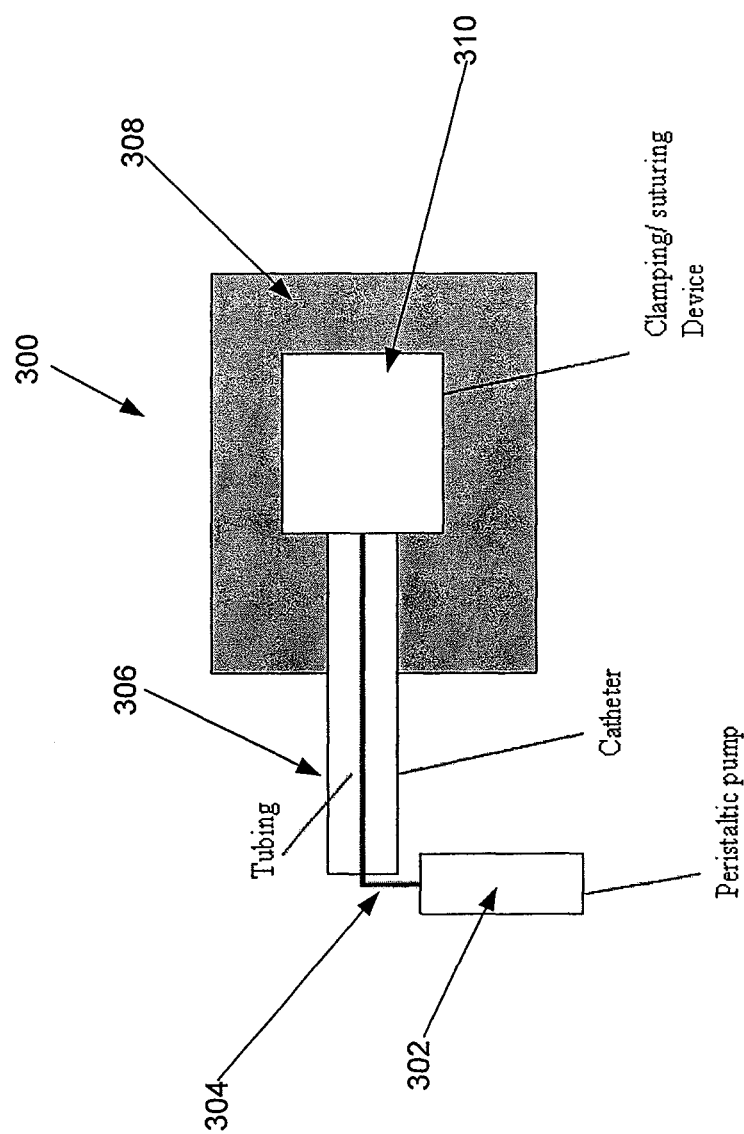
FIG. 13 is a block diagram of the components driving the clamping system of the present invention.

Referring to FIG. 13, the peristaltic pump 302 will produce a pressure that will be utilized to manipulate the mechanical parts in the device. Depending on the action, both negative and positive pressures will be required to manipulate the suturing and the clamping of the annulus. As illustrated in FIG. 13, tubing 304 which extends through the catheter 306 will transmit pressure to the clamping device 310. The clamping device 310, composed of multiple pressure channels, responds to pressure variations by miniature solenoid hydraulic pistons within the device. The pistons need to resist the high pressures. Tygon® 2275, manufactured by Saint-Gobain™ Corporation or, preferably, silicone tubules would withstand the pressures transmitted to the device, and are also manufactured for sterility purposes. The tubing 304 can be cleaned by radiation, chemicals like ethylene oxide, or by steam, which are common methods of ensuring sterilization for surgical instruments.

Figure 14A:
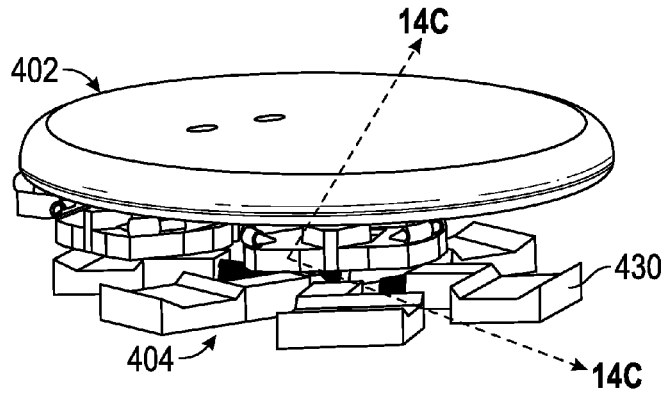
FIG. 14A is a clamping assembly of the present invention.
Figure 14B:
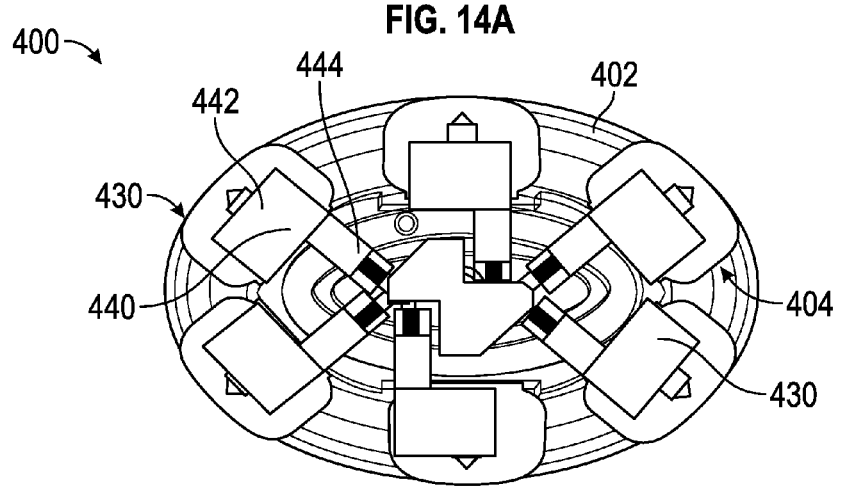
FIG. 14B is a bottom view of the clamping assembly illustrated in FIG. 14A.
Figure 14C:
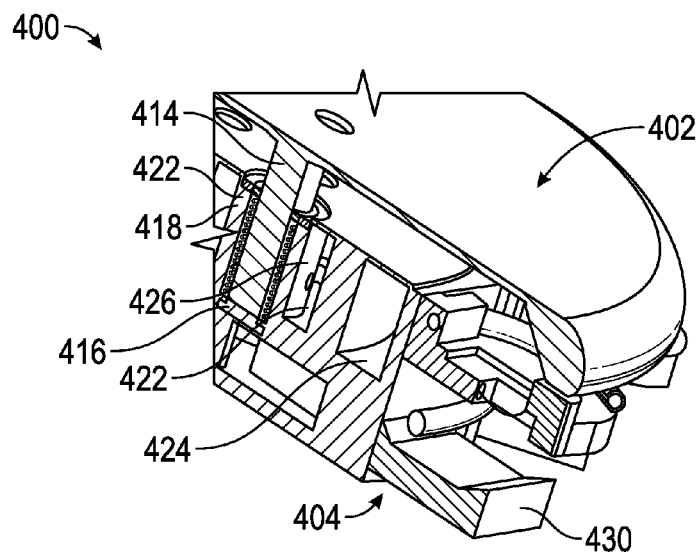
FIG. 14C is a sectional view of a portion of the clamping assembly illustrated in 14A.

The clamping mechanism, shown in FIGS. 14A, 14B and 14C, is made up of two subassemblies: one subassembly for the top clamp 402 and a second subassembly for the bottom clamp 404. Clamping is used to "pinch" the native annulus of the patient so that the suturing device is stable during suturing. More importantly, clamping guides the surgeon, using the echocardiogram to position the device properly and safely inside the heart. It is the only "visual" guide, since the device's dense material properties compared and the annulus—which is made of dense fibers can be observed though imaging. A perspective view of the clamping mechanism 400 is shown in FIG. 14A. A bottom view of the clamping mechanism 400 is shown in FIG. 14B.

Figure 14E:
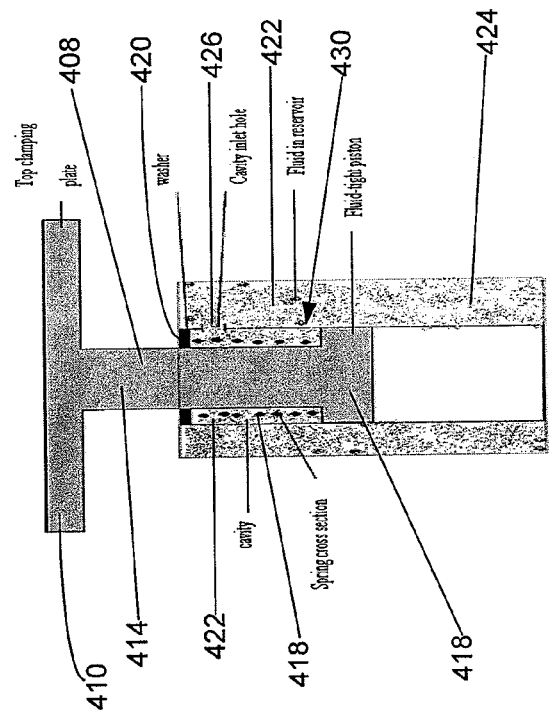
FIG. 14E is a cross sectional view of the piston assembly of the top clamping plate of FIG. 14D.
Figure 14D:
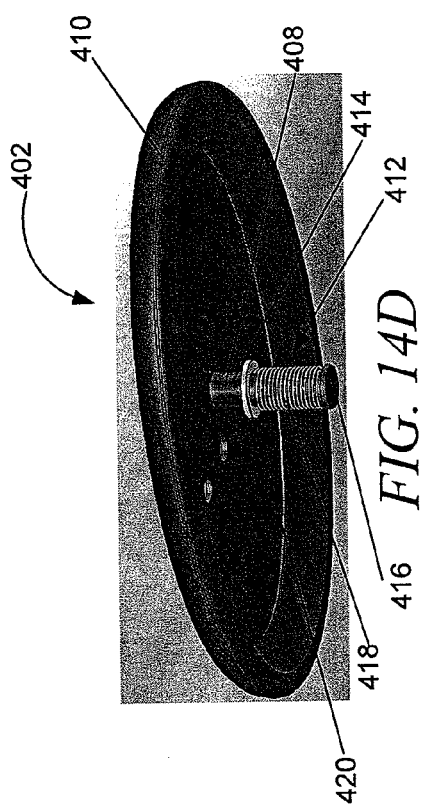
FIG. 14D is an illustration of the top clamping plate of the clamping assembly illustrated in FIG. 14A.

The top clamping subassembly 402, as illustrated in FIG. 14D includes a mushroom like plate with rounded edges 410, a piston assembly 412, which in this embodiment includes a piston 408 that is about 4 mm long, a spring 418 and washer 420 attached to the piston 408. As illustrated in FIG. 14E, the piston 408 is comprised of two parts, a top piston portion 414 and a bottom piston portion 416. The bottom piston portion 416 has a larger circular bottom and begins about at 3.5 mm from the top of the piston 408. Referring to FIG. 14D, the piston assembly 412 is shown in a clamped down position.

As illustrated in FIG. 14E, the clamping mechanism works when fluid pressure in piston cavity 422 changes. Increased pressure from reservoir 424 causes water to flow into the piston cavity 422 through a cavity inlet 426, which in the present embodiment is a 0.5 mm hole on the cylindrical surface 430 of the reservoir 424. Increased cavity pressure forces the piston 408 down, resulting in a 3 mm displacement of the top clamp plate 410 to within 1 mm distance from the suturing subassembly at the curved and rounded ends. The washer 420 is permanently attached to the piston 408 to prevent the piston 408 from ejecting off under pressure.

Conversely, when fluid pressure in reservoir 424 is decreased, fluid rushes off from the cavity 422, resulting in relaxation of the torsion spring 418 and subsequent rise of the top clamp plate 410, or unclamped position of the clamping mechanism 400. The piston cavity 422 has a capacity of 32 mm³ when the torsion spring 418 is stretched to maximum 3.5 height of the piston cavity 422 barrel and a minimum capacity of about 12.00 mm³ when piston 408 is pulled up by the torsion spring 418 when the torsion spring 418 is relaxed. The torsion spring 418 is displaced by 3 mm. The properties of the torsion spring were determined by the Equation $$k = \frac{1}{f}$$

where f is the flexibility of the torsion spring 418, given by displacement-force ratio. A torsion spring 418 of with k value of 34.0 K/m is required for the top clamp plate 410 of the present embodiment.

Unlike the top clamping assembly 402, the bottom clamping assembly 404 illustrated in the present embodiment is made up of six similar subassemblies 430, each one 3 mm below the suturing subassemblies. Because of the general tapered shape of the inside of a right atrium within a heart, it was determined that the most effective way to secure the annulus in a proper suturing position was to stabilize the bottom of the entire device 400 by horizontally pressing the bottom clamps 404 to the walls of the heart just below the native annulus. This avoids tearing parts of the tricuspid leaflet by any actuation from the device 400. For a patient with prolapsing leaflets, chances of bruising the leaflets are even higher as it protrudes into the atrium. The bottom clamps 404 are moved horizontally like a solenoid from inside of the device 400. To unclamp, the bottom clamps 404 are retracted into the device 400.

As illustrated in FIG. 14B, the larger tissue-clamping end of each of the clamps is 6.5 mm wide, and they are all arranged in an oval shape, mimicking the general shape of the device and heart. The clamps extend by 3.7 mm, which results in the expansion of the bottom part of the device by about 7 mm diameter (both short and long diameters). This extension, which is triggered after the device 400 has been positioned causes stabilization of the device 400 inside the atrium and also aids is exposing the native annulus into the suturing subassembly.

In the embodiment illustrated, in FIG. 14B, clamps 440 that are L-shaped, are wider 442 on the outside (6.5 mm) and narrower 444 on the inside (2.5 mm). The narrow section 444 is the piston part of the clamps that is pressed by increased fluid pressure from reservoir 424. The clamps 440 are spring loaded. Increased fluid in the reservoir 424 enters the cavities that hold the clamps, causing extension of the clamps 440. The spring's 418 purpose is to maintain smooth clamp extension, and more importantly, ensure retraction of the clamp.

Referring to FIGS. 15A, 15B, and 15C, a suturing subassembly 460 is illustrated, which includes a needle 462, a silicon bed 464, and a fluid channel 466 connected to the fluid reservoir 422 and a main reservoir 484. During operation of the suturing sub-assembly 460, fluid from a pump enters the suturing sub-assembly 460 by a tubule 470 into a main reservoir 468. Increased pump reassure within the main reservoir 468 transmits hydrostatic pressure through fluid channel 466. The needle 462, which has a configuration of a C is pressed to curve around through the annulus into the silicone bed 464. At the silicone bed 464, the needle goes through a slip knot before it gets stuck. The device 400 is then unclamped and removed.

The suturing mechanism shall be comprised of a plurality of needles. One embodiment shall be comprised of twelve needles in six subassemblies. The geometric design of the needle 462 is configured to ensure that the needle 462 does not curve and get driven into the adjacent subassembly. In alternative embodiments, individual needles may be provided per suturing subassembly.

In one embodiment, the main reservoir 468 shall include an estimated volume of 531.06 mm$^3$ and be connected with one inlet having a 1.5 mm diameter tubule 470 connected to an external pump and six 0.5 mm diameter channels connected to each of the suturing units. In the suturing units, the channels are further subdivided into two for each, making 12 end channels, each with 0.5 mm diameter.

In one embodiment, knotted sutures are used to attach annuloplasty implant ring to the annulus. The suture points would be the points on the native annulus where the needle-suture sub-assembly will act on to stitch the artificial ring to. To help understand the general principle behind the knotting technique used in the needle-suture sub-assembly a real world example will be considered. The way the knotting mechanism works is similar to the means by which a snare operates. A snare is comprised of a single piece of rope, wherein one end is looped using a simple slip knot. As the desired object trips the snare, the loop closes around the object, by drawing the rope in one direction effectively closing the loop around the object. The knotting mechanism operates under the same principle, wherein the object being caught is the other end of the rope, where the needle will be attached. The most crucial aspect of this design is that, first the needle goes through the loop, and second the loop must be a sufficient size as to close in time with when the needle is stopped from moving in its previous direction. This is accomplished by making the length of the circumference of the loop the exact length the needle shall move from its starting position to its final destination, the silicon bed for the purposes of this design.

A slip knot was used to accomplish the predefined task. For the purposes of the design the exact material considered for the suture is silk, as it is the most common type of suture used to perform the current surgery. The silk wire is approximately 0.35 mm in diameter. The needle attached to the end is slightly curved, with a radius of curvature of 3.43 mm; this specific curvature was considered as it allows for the needle to pass through the annulus, when the mechanism is implemented, more easily. In addition to allowing for the needle curvature of the needle to help maintain the desired curved path to the final destination of the needle. The needle is attached to the silk wire by means of a manufacturing process wherein the needle is formed around, or pressed onto the silk wire effectively affixing itself to it. This provides for the needle not coming undone from the silk wire in use and the ability to apply a relatively high stress at the end of the needle without detaching the silk wire from the needle. The details of the construction of the needle to the silk, or how the silk is formed or twisted into the wire maybe found through the manufacturer, in this case Ethicon, a division of Johnson and Johnson. Note is it imperative that the material chosen for the design is one that is bio-compatible, otherwise the body would instantly reject the material, or the probability of infection greatly increases.

Excess suture ends will need to be cut off from the device. While conclusions on this will depend largely on the suture pulling mechanism, a preliminary sliding plate has been chosen. The plate, will consist of a sliding plate with holes in it. Suture ends will come out of the holes. The sliding plate's holes will have sharp edges that would cut off the suture once slid against the stationary plate. Since this procedure will be performed after unclamping the device, the same hydraulic actuator as illustrated in FIG. 15A, that is used to clamp would be used to create pressure that is required to slide the moveable plate.

Reference may be made throughout this specification to "one embodiment," "an embodiment," "embodiments," "an aspect," or "aspects" meaning that a particular described feature, structure, or characteristic may be included in at least one embodiment of the present invention. Thus, usage of such phrases may refer to more than just one embodiment or aspect. In addition, the described features, structures, or characteristics may be combined in any suitable manner in one or more embodiments or aspects. Furthermore, reference to a single item may mean a single item or a plurality of items, just as reference to a plurality of items may mean a single item. Moreover, use of the term "and" when incorporated into a list is intended to imply that all the elements of the list, a single item of the list, or any combination of items in the list has been contemplated.

One skilled in the relevant art may recognize, however, that the invention may be practiced without one or more of the specific details, or with other methods, resources, materials, etc. In other instances, well known structures, resources, or operations have not been shown or described in detail merely to avoid obscuring aspects of the invention.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the claimed invention.

The above specification, examples and data provide a description of the manufacture and use of the invention. Since many embodiments of the invention can be made without departing from the spirit and scope of the invention, the invention resides in the claims hereinafter appended.

We claim:
1. An apparatus for implantation of an annuloplasty implant into the heart of a patient, the apparatus comprising:
    a unitary tube comprising a distal end, a proximal tube portion, a distal tube portion and a transition region disposed there between, the unitary tube further comprising an exterior surface defining an outside diameter, an interior surface defining an inside diameter of the unitary tube;
    a guide assembly controller; and
    an annuloplasty implant guide assembly comprising:
        a suturing sub-assembly system configured to deploy a plurality of suture hooks that connect the annuloplasty implant to tissue within the heart, and
        an external clamping assembly configured to resize a valve annulus by applying an external pressure to an external circumference of an annular region of the heart of the patient, wherein the external clamping assembly comprises at least one of:
            a top clamp plate comprising a piston assembly configured to reduce spacing between the top clamp plate and a bottom clamp plate, the bottom clamp plate comprising a plurality of subassemblies configured to position the bottom clamp plate to walls of the heart below the valve annulus, the plurality of subassemblies being configured to extend from the bottom clamp plate by pressure in the piston assembly, and an external trocar that surrounds the mitral annular orifice and temporarily reduces it in size to enable internal deployment of a ring of a smaller size than the annulus;

wherein the annuloplasty implant guide assembly is attached to the distal end of the unitary tube; and wherein the proximal tube portion includes the guide assembly controller being operatively connected to the annuloplasty implant guide assembly by a control mechanism that extends from the guide assembly controller through the interior of the unitary tube to the annuloplasty implant guide assembly.

2. The apparatus of claim 1 wherein each of the plurality of suture hooks is releasably attached to the suturing sub-assembly system and comprised of a first hook arm and a second hook arm, wherein the first and second hook arms are both pivotally connected at a first end by a pivot pin, wherein the second ends of the first and second hook arms are configured to be extended through tissue of an annulus wall within a heart valve and extended through an annuloplasty implant, thereby connecting the annuloplasty implant to the annulus of a valve, the second ends of the first and second hook arms being connected in a manner that latches the second ends of the first and second hook arms and thereby creates a substantially continuous closed loop.

3. The apparatus of claim 1 wherein the distal end of the unitary tube includes an orientation member configured to facilitate rotation of the annuloplasty implant guide assembly and the annuloplasty implant in all directions in response to manipulation of the guide assembly controller.

4. The apparatus of claim 3 wherein the suturing sub-assembly further includes a deployment mechanism extending through the interior surface of the unitary tube, wherein the deployment mechanism facilitates deployment of each of the plurality of suture hooks and thereby connecting the annuloplasty implant to the inner tissue of the heart cavity into which the annuloplasty implant is inserted.

5. The apparatus of claim 1 wherein an incision cover assembly is attached to the exterior surface of the unitary tube, wherein the incision cover comprises a umbrella skeleton covered by a biocompatible incision cover material, wherein the umbrella skeleton is connected to the exterior surface of the unitary tube by a deployment ring positioned around the exterior surface of the unitary tube and configured to slide up and down the unitary tube exterior surface causing the umbrella skeleton and thereby the incision cover to retract and deploy.

6. The apparatus of claim 1 wherein the annuloplasty implant guide assembly has an annular shape and contains a suturing sub-assembly, wherein the suturing sub-assembly includes a plurality of suture hooks configured to detach from the suturing sub-assembly and connect the annuloplasty implant to the inner tissue of the heart cavity into which the apparatus is inserted.

7. The apparatus of claim 1 wherein the distal end of the unitary tube includes an orientation member configured to facilitate rotation of the annuloplasty implant guide assembly in a manner such that its longest side is perpendicular with the plane of the body into which an incision has been made.

8. The apparatus of claim 1 wherein the annuloplasty implant guide assembly is comprised of a plurality of arms each of which are attached to the annuloplasty implant being delivered to the heart.

9. The apparatus of claim 1 wherein the annuloplasty implant guide assembly is configured to facilitate folding of the annuloplasty implant in order to facilitate passing the annuloplasty implant through an incision having a size smaller than necessary when the annuloplasty implant is not folded.

10. The apparatus of claim 1 wherein the suturing sub-assembly system includes a plurality of pumps, wherein the pumps comprise at least one of a microfluidic pump and a microelectromechanical pump, wherein each of the plurality of pumps is operatively connected to at least one of the plurality of suture hooks, wherein the pumps control deployment of the suture hooks in a manner connecting the annuloplasty implant to the inner tissue of the heart cavity into which the annuloplasty implant is inserted.

11. The apparatus of claim 1 wherein the suturing sub-assembly system is configured to enable a user to control deployment of the plurality of suture hooks in any manner desired by the user, including deploying each of the plurality of suture hooks individually, deploying each of the plurality of suture hooks in groups and deploying each of the plurality of suture hooks all at once.

12. The apparatus of claim 1 wherein the annuloplasty implant guide assembly includes an adjustable mounting system onto which annuloplasty rings of a plurality of different shapes, rigidity and sizes may be mounted.

13. The apparatus of claim 1, wherein positioning of the annuloplasty implant guide assembly and deployment of suture hooks by the suturing sub-assembly is guided by at least one of a plurality of methods including medical imaging modalities and direct visualization through blood using at least one infrared cameras mounted on the annuloplasty implant guide assembly.

14. The apparatus of claim 1, wherein movement of the annuloplasty implant guide assembly and control of the suturing sub-assembly may be controlled by a software module that allows the user to activate and deactivate components of the apparatus including at least the components comprising the annuloplasty implant guide assembly and the components comprising the suturing sub-assembly.

15. The apparatus of claim 1 wherein the apparatus is integrated with a surgical robot allowing the user to control the apparatus by way of the surgical robot.

16. The apparatus of claim 1, wherein secondary devices, including at least one of artificial heart valves and tissue engineering heart valves, may be delivered to the site of the annuloplasty implant through the unitary tube following implantation of the annuloplasty implant into the heart, wherein the secondary devices may be deployed onto the previously implanted annuloplasty implant using the annuloplasty implant guide assembly already in position as a result of the implantation of the annuloplasty implant.

17. A method of implanting an annuloplasty implant, comprising:

providing an apparatus for implantation of an annuloplasty implant that includes an annuloplasty implant guide assembly configured with at least one annuloplasty implant connector;

resizing a heart valve annulus by applying an external pressure to an external circumference of an annular region of a heart of a patient utilizing a clamping assembly comprising at least one of:

a top clamp plate comprising a piston assembly for reducing spacing between the top clamp plate and a bottom clamp plate, the bottom clamp plate comprising a plurality of subassemblies configured for positioning the bottom clamp plate to walls of the heart below the valve annulus the plurality of subassemblies extending from the bottom clamp plate by pressure in the piston assembly, and an external trocar that surrounds the mitral annular orifice and temporarily reduces it in size to enable internal deployment of a ring of a smaller size than the annulus;

connecting the annuloplasty ring to the at least one annuloplasty implant connector of the implant guide assembly;

adjusting the orientation of the implant guide assembly and thereby the orientation of the annuloplasty implant, wherein the adjusted orientation of the annuloplasty implant facilitates passing the annuloplasty implant through an incision on a patient's body having a size smaller than necessary when the annuloplasty implant orientation is not adjusted;

extending the orientation adjusted guide assembly and the annuloplasty ring through the incision;

readjusting the orientation of the guide assembly and thereby the orientation of the annuloplasty ring after the orientation adjusted guide assembly extends through the incision;

positioning the annuloplasty ring within the resized heart valve annulus; and initiating an automatic suture procedure wherein at least one of a plurality of suture connection rings extends through tissue of the heart valve annulus and the annuloplasty ring thereby connecting the annuloplasty ring to the heart valve annulus.

18. The method of claim 17 wherein the positioning of the annuloplasty implant ring within a heart valve annulus causes a reshaping of the heart valve annulus, wherein reshaping comprises at least one of changing the heart valve geometry and changing the heart valve size.

19. The method of claim 17 wherein the apparatus for implantation of an annuloplasty implant includes a hollow unitary tube connected to the annuloplasty implant guide assembly, wherein the method includes the step of delivering secondary devices through the unitary tube to the implanted annuloplasty ring which serves as a platform that can support implantation of the secondary devices within the heart valve annulus.

* * * * *